United States Patent
Kasuya

(10) Patent No.: US 7,111,984 B2
(45) Date of Patent: Sep. 26, 2006

(54) X-RAY COMPUTED TOMOGRAPHY APPARATUS WITH HEAT EMISSION SYSTEM

(75) Inventor: Yuichi Kasuya, Tochigi-ken (JP)

(73) Assignees: Kabushiki Kaisha Toshiba, Tokyo (JP); Toshiba Medical Systems Corporation, Otawara (JP)

(\*) Notice: Subject to any disclaimer, the term of this patent is extended or adjusted under 35 U.S.C. 154(b) by 96 days.

(21) Appl. No.: 10/753,536

(22) Filed: Jan. 9, 2004

(65) Prior Publication Data

US 2004/0196955 A1 Oct. 7, 2004

(30) Foreign Application Priority Data

Jan. 10, 2003 (JP) ............... 2003-004178

(51) Int. Cl.
*A61B 6/00* (2006.01)
*H02P 3/14* (2006.01)

(52) U.S. Cl. ............... 378/199; 378/204; 378/4; 318/376; 165/53

(58) Field of Classification Search ............. 378/4–20; 165/61, 53–57, 69; 318/375, 376; 219/759
See application file for complete search history.

(56) References Cited

U.S. PATENT DOCUMENTS

| | | | | |
|---|---|---|---|---|
| 3,704,359 A | * | 11/1972 | Laing ............... | 219/213 |
| 4,513,053 A | * | 4/1985 | Chen et al. ............... | 428/221 |
| 4,658,408 A | * | 4/1987 | Amor et al. ............... | 378/4 |
| 4,723,259 A | * | 2/1988 | Amor et al. ............... | 378/10 |
| 4,896,831 A | * | 1/1990 | Choi ............... | 237/69 |
| 5,097,495 A | * | 3/1992 | Gray et al. ............... | 378/117 |
| 6,289,073 B1 | * | 9/2001 | Sasaki et al. ............... | 378/4 |
| 6,430,045 B1 | * | 8/2002 | Everitt ............... | 361/690 |
| 6,721,388 B1 | * | 4/2004 | Tybinkowski et al. ............... | 378/17 |

FOREIGN PATENT DOCUMENTS

JP 2002-336236 11/2002

OTHER PUBLICATIONS www.filnor.com, "Home" "Power Resistors", "Grid Resistors & Parts," "Helicoil Resistors," and "Enclosure Assemblies," May 25, 2002, via Internet Archive Wayback Machine.*
www.filnor.com, "Dynamic Braking Resistors," "Grid Resistors," "Helicoil Wirewound Resistors," and "Smooth Wirewound Resistors," Aug. 10, 2002 via Internet Archive Wayback Machine.*

\* cited by examiner

*Primary Examiner*—Edward J. Glick
*Assistant Examiner*—Krysytna Suchecki
(74) *Attorney, Agent, or Firm*—Oblon, Spivak, McClelland, Maier & Neustadt, P.C.

(57) ABSTRACT

An X-ray computed tomography apparatus wherein an X-ray is generated by a generator and an X-ray data resulting from the X-ray is detected by a detector. The apparatus includes a supporter, a driver, a body, and a converter. The supporter is configured to support the generator and the detector. The driver is configured to drive the supporter. The body is configured to incorporate the supporter and the driver. The converter is provided at a bottom of the body and is configured to convert regenerative energy caused by the driver to heat energy.

8 Claims, 5 Drawing Sheets

X-RAY COMPUTED TOMOGRAPHY APPARATUS WITH HEAT EMISSION SYSTEM

CROSS-REFERENCE TO RELATED APPLICATION

This application is based upon and claims the benefit of priority from prior Japanese Patent Application No. P2003-4178, filed on Jan. 10, 2003, the entire contents of which are incorporated herein by reference.

BACKGROUND OF THE INVENTION

1. Field of the Invention

The present invention relates to an X-ray computed tomography apparatus with a heat emission system that emits heat regenerated in resistors and further relates to the heat emission system.

2. Discussion of the Background

Recently, medical diagnosis devices have been improved outstandingly. Particularly, various techniques have been introduced in the field of an X-ray computed tomography apparatus (hereinafter referred to as a CT apparatus), which uses an X-ray to tomograph an examination object or a patient (hereinafter referred to as a specimen). In addition, a tomography time has been reduced more than before.

In such a technical innovation, an issue that is always considered is how to emit heat caused collaterally in the CT apparatus. It is a fact, however, that the heat needed to be emitted increases as the CT apparatus is improved. Therefore, this is one of several serious problems related to development of a further improved CT apparatus as well as for a current CT apparatus.

One well-known type of heat, which is caused inside the CT apparatus, is heat generated by regenerative resistors. In the CT apparatus, a motor, such as, for example, a direct drive motor or a rotation servo-motor, drives a rotation ring that rotates for tomographing a specimen. When a rotation speed of the rotation ring is reduced, back electromotive force energy is generated. The regenerative resistors are provided for converting the back electromotive force energy into heat energy.

Therefore, when acceleration and deceleration of the rotation speed are alternately repeated so often by the motor, the regenerative resistors sometimes reach a high temperature (e.g., 70° Celsius). Such repetition may occur, for example, when a lot of specimens are continually tomographed or when a field engineer implements a maintenance service on the CT apparatus.

One solution for the above issue is an increase of the number of the regenerative resistors. Other proposed solutions are described below as examples.

One type of the CT apparatus has an orthogonally shaped gantry in a view from a front side of the CT apparatus. In such a CT apparatus, one or more regenerative resistors are provided at a top of the gantry so as to easily emit heat from the regenerative resistors. Further, the regenerative resistors contact with a sheet metal provided in the gantry so as to let out the heat through the sheet metal. This type of CT apparatus may be replaced by the following type of CT apparatus, considering a psychological burden on the specimen.

Another type of CT apparatus has a gantry with a top in a shape of an arc so as to present a moderate impression. This configuration may reduce the discomfort experienced by a specimen. In such a CT apparatus, it is difficult to keep an enough space to provide the regenerative resistors at a top of the gantry. Therefore, the regenerative resistors are often provided at one or more sides of the CT apparatus.

In this type of CT apparatus, a fan or the like is additionally provided and used to guide heat caused by the regenerative resistors to the outside of the CT apparatus. For example, Japanese Patent Application Publication No. PH9-276262 describes a CT apparatus, which has a suction opening at an upper side of a gantry opening and a cooling fan at a top of the gantry. Accordingly, an air stream is caused through the suction opening and the cooling fan, which results in heat emission.

A further example of using a fan is described in Japanese Patent Application Publication No. PH9-56710. In this example, a CT apparatus includes a supporting member with a plurality of blade members. These blade members are rotated with a rotation ring so as to send air to emit heat inside the CT apparatus. Similar to the example of Japanese Patent Application Publication No. PH9-276262, this example emits heat by ventilating an inside of the CT apparatus.

Still further, a CT apparatus described in Japanese Patent Application Publication No. P2002-336236 includes a regenerative resistor unit and a ventilation fan. The regenerative resistor unit is provided inside a gantry. The ventilation fan provides a bed where a specimen lies with heat caused by the regenerative resistor unit. This helps to warm the specimen. Also similar to the example of Japanese Patent Application Publication No. PH9-276262, this example emits heat by using an air stream.

As described above, various techniques have been introduced for solving the heat issue. On the other hand, tomography time reduction is still being challenged for reducing more the discomfort and X-ray exposure of the specimen.

This challenge means reduction of scanning time. For the reduction of the scanning time, it is necessary to rotate a rotation ring, which is used for tomography, much faster. Since the rotation ring is driven by the motor, the motor is required to be accelerated and decelerated more quickly. This results in generation of a larger amount of regenerative energy, compared to the heat generated before. Accordingly, a larger amount of heat energy is generated by regenerative resistors.

Such a large amount of heat energy cannot be adequately released by the above-described techniques disclosed in the Japanese Patent Application Publications. If the heat emission does not function well, the temperature goes up inside the CT apparatus, so that defective performance may be caused in various precision devices provided in the CT apparatus.

As the above-described CT apparatus having a top in a shape of an arc, regenerative resistors may be provided at sides of a CT apparatus. In this case, if a doctor or a radiological technologist passes by the CT apparatus for taking care of a specimen lying on a bed, the doctor or the radiological technologist may happen to touch the regenerative resistors (or a body part of the CT apparatus incorporating the regenerative resistors) by accident and be burned. Similarly, a field engineer may happen to touch the regenerative resistors by accident during maintenance service and be burned.

If action is taken for safety in the above burning case, the CT apparatus may require a complex configuration and/or a high cost in manufacture. For example, the CT apparatus may need to include a function of effectively lowering the temperature of the regenerative resistors. Further, the CT apparatus may need a function of avoiding heat conduction to a body surface of the CT apparatus.

SUMMARY OF THE INVENTION

According to a first aspect of the present invention, there is provided an X-ray computed tomography apparatus wherein an X-ray is generated by a generator and an X-ray data resulting from the X-ray is detected by a detector. The apparatus includes a supporter, a driver, a body, and a converter. The supporter is configured to support the generator and the detector. The driver is configured to drive the supporter. The body is configured to incorporate the supporter and the driver. The converter is provided at a bottom of the body and is configured to convert regenerative energy caused by the driver to heat energy.

According to a second aspect of the present invention, there is provided a heat emission system provided at a bottom of an apparatus. The system is connected to an element provided in the apparatus which cause regenerative energy as a result of a predetermined operation. Further, the system includes a converter. The converter is configured to convert the regenerative energy to heat energy. The converter is further configured to contact a floor where the apparatus is placed.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DESCRIPTION OF THE PREFERRED EMBODIMENTS

Embodiments of the present invention will be described with reference to the accompanying drawings.

(First Embodiment)

Figure 1:
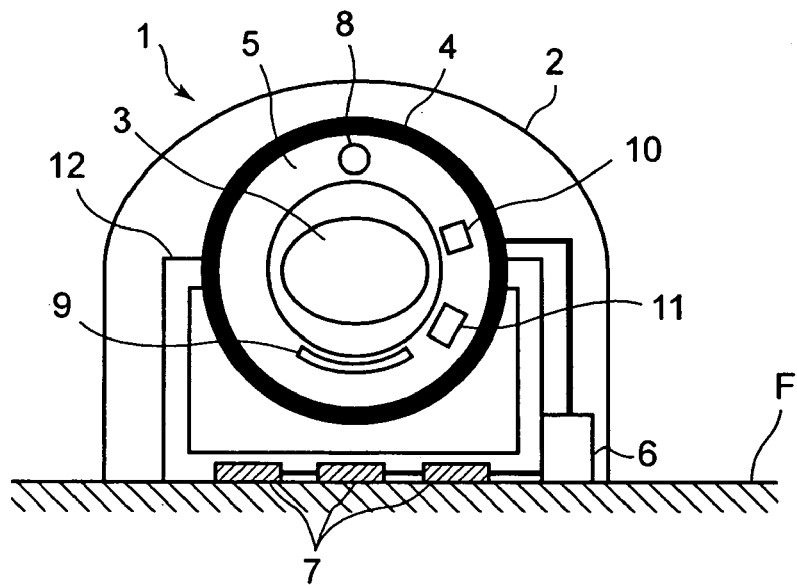
FIG. 1 is an illustration showing an exemplary configuration of a CT apparatus according to a first embodiment of the present invention.

FIG. 1 is an illustration showing an exemplary configuration of a CT apparatus 1 according to a first non-limiting embodiment of the present invention. FIG. 1 shows a perspective view from a front of the CT apparatus 1. The CT apparatus 1 implements scanning for a specimen in which an X-ray is radiated to the specimen and detects a transmission X-ray transmitted from the specimen. Although not shown in FIG. 1, the CT apparatus may be used as a part of an X-ray computed tomography system. The X-ray computed tomography system usually includes a patient couch, a processor, and a display. The patient couch includes a table where the specimen lies. The patient couch moves the bed and brings the specimen into a tomography opening provided in the CT apparatus 1. The processor includes a computer for implementing a reconstruction processing on detected data obtained from the CT apparatus 1. The display may be a part of the computer and displays the reconstructed data as an image (or as an X-ray computed tomograph).

The CT apparatus 1 includes, for example, a body 2, a tomography opening 3, a motor 4, a rotation ring 5, a servo-amplifier 6, regenerative resistors 7, an X-ray tube 8, a detector 9, a power source unit 10, a signal processor 11, and a gantry stand 12. The CT apparatus 1 is placed on a floor F. The body 2 is a housing of the CT apparatus 1. The tomography opening 3 is an opening provided near a center of the body 2. The specimen lying on the bed is brought into the tomography opening 3 for tomography. The motor 4 is, for example, a direct drive motor and is an example of a driver. The rotation ring 5 is provided to circumscribe the tomography opening 3 and rotated by the motor 4. The rotation ring 5 incorporates the X-ray tube 8, the detector 9, the power source unit 10, and the signal processor 11. The rotation ring 5 is an example of a supporter, which supports the X-ray tube 8 and the detector 9. The X-ray tube 8 is an example of a generator.

Further, the servo-amplifier 6 adjusts a power voltage and a frequency to be supplied to the motor 4 based on signals supplied from a motor control unit (not shown in FIG. 1). Accordingly, the servo-amplifier 6 controls driving and stopping the motor 4. The servo-amplifier 6 further controls the motor 4 to change a rotation speed of the rotation ring 5.

Electric energy is caused at a time of deceleration of the motor 4. The electric energy flows back to the servo-amplifier 6 as regenerative energy. The regenerative resistors 7 are, for example, made of cement and convert the electric energy (the regenerative energy) to heat energy and consume the heat energy. Although one or more regenerative resistors are provided in the servo-amplifier 6, some energy is not totally consumed by the regenerative resistors inside the servo-amplifier 6. Therefore, the regenerative resistors 7 are used for consuming the remaining energy (i.e., the energy which has not been consumed by the regenerative resistors inside the servo-amplifier 6). The regenerative resistors 7 may be provided at the bottom of the body 2 and may contact a floor F or other surface. At the bottom of the body 2, the regenerative resistors 7 are also inserted into and placed in an opening space of the gantry stand 12. Still further, the regenerative resistors 7 may be placed a predetermined distance away from each side of the body 2, so that heat generated cannot be transferred to the sides of the body 2.

The X-ray tube 8 radiates (or generates) an X-ray. The detector 9 is placed opposite the X-ray tube 8 and detects the X-ray radiated from the X-ray tube 8. The power source unit 10 supplies power to the X-ray tube 8 and the detector 9. The signal processor 11 processes a detection result obtained from the detector 9. The gantry stand 12 includes a supporter vertically provided to support the motor 4 and the rotation ring 5. The gantry stand 12 is usually made of steel plate, for example.

Operations of an X-ray computed tomography system including the CT apparatus 1 are basically implemented in the following manner. The motor 4 is supplied with power from the servo-amplifier 6 and rotates the rotation ring 5. While the rotation ring 5 is rotating, the X-ray tube 8 radiates an X-ray. The specimen is exposed to the radiated X-ray when the specimen is inserted into the tomography opening 3. A transmission X-ray (or X-ray data) transmitted from the specimen is detected by the detector 9. The X-ray tube 8 and the detector 9 are supplied with power from the power source unit 10. The detected transmission X-ray is processed and produced as image raw data by the signal processor 11. The raw image data are transferred to the above-described computer. The computer implements an image reconstruction processing on the raw image data so as to produce image data. The image data are displayed as an image of the specimen.

When such a tomography operation described above is repeated often, back electromotive force energy (i.e., regenerative energy) is generated due to deceleration of the motor 4. This regenerative energy is transferred to the regenerative resistors 7 and converted into heat energy. Accordingly, the temperature of the regenerative resistors 7 increases due to the heat energy. The heat is emitted to their periphery by two possible routes. One possible route of the heat emission is through the gantry stand 12, a part of which contacts or is close to top surfaces of the regenerative resistors 7. Another possible route of emission is through the floor F with which regenerative resistors 7 are in contact.

The floor F is, for example, made of concrete. Since the concrete has a relatively large specific heat and a high mass, its heat capacity is very large. In addition, the temperature of the concrete is generally lower than that of the regenerative resistors 7 emitting the heat. Therefore, the heat generated by the regenerative resistors 7 is efficiently conducted to the floor F.

The floor F is not a part of the CT apparatus 1, but is situated outside the CT apparatus 1 so that the heat emitted to the floor F can be ignored in influence on an environment inside the CT apparatus 1. It becomes possible to effectively emit the heat of the regenerative resistors 7 to the outside of the CT apparatus 1, by making the regenerative resistors 7 to contact with the floor F. This results in avoiding a rise of the temperature inside the body 2, which is helpful to prevent various units such as, for example, the X-ray tube 8 and the detector 9, from deteriorating in functionality due to the heat. The floor F may alternatively be made of metal, such as, for example, iron.

Compared to the conventional air cooling type heat emission techniques, the direct contact of the regenerative resistors 7 with the floor F makes it possible to more efficiently emit the heat to the outside of the CT apparatus 1. Further, placing the regenerative resistors 7 a predetermined distance away from the sides of the body 2 can be helpful for highly reducing a risk that the doctor, the radiological technologist, or the field engineer touches the regenerative resistors 7 by accident and gets burned.

Still further, since many types of popular CT devices already have an empty space at the bottom of the devices, it may be possible to provide regenerative resistors in the empty space without changing the positioning of other units. Particularly, by preparing an opening in a gantry stand and placing regenerative resistors in the opening, it can be possible to accomplish the configuration according to the first embodiment without changing positions of units provided in a CT apparatus at all. Therefore, there is no difficulty in designing the CT apparatus. Also it is possible to accommodate various requirements without much difficulty, such as, for example, changing positions of regenerative resistors in an existing CT apparatus or providing regenerative resistors in an existing CT apparatus.

(First Modification)

Figure 2:
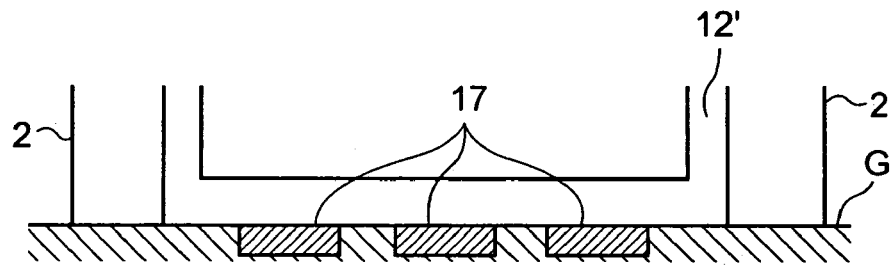
FIG. 2 is an illustration showing a first modified configuration example of the CT apparatus according to the first embodiment of the present invention.

According to the first non-limiting modification of the first embodiment, regenerative resistors are provided in the CT apparatus 1 in a different manner from the embodiment shown in FIG. 1. FIG. 2 is an illustration showing the first modified configuration example of the CT apparatus according to the first embodiment of the present invention.

As shown in FIG. 2, regenerative resistors 17 are provided at the bottom of the CT apparatus 1. Unlike the CT apparatus 1 shown in FIG. 1, top surfaces of the regenerative resistors 17 contact a bottom surface of a gantry stand 12'. The regenerative resistors 17 also project from the bottom of the CT apparatus 1. In this case, a floor G where the CT apparatus 1 is placed is processed to accommodate the projecting regenerative resistors 17.

In the above configuration of the CT apparatus 1 with the fitting floor G, the regenerative resistors 17 contact the floor G in a larger contact area than the regenerative resistors 7 in FIG. 1. Therefore, the heat generated by the regenerative resistors 17 can be transferred more efficiently to the floor G.

(Second Modification)

Figure 3:
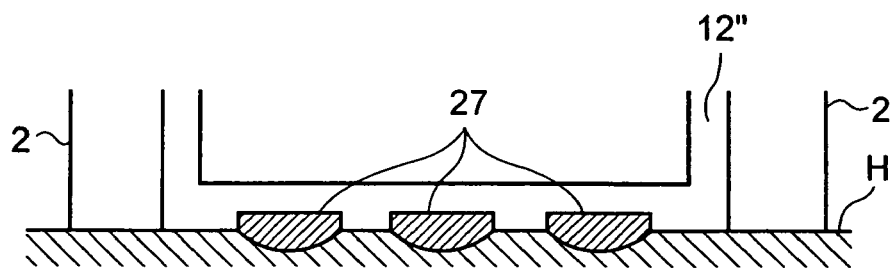
FIG. 3 is an illustration showing a second modified configuration example of the CT apparatus according to the first embodiment of the present invention.

A further non-limiting modification of the CT apparatus 1 will be described with reference to FIG. 3. FIG. 3 is an illustration showing a second modified configuration example of the CT apparatus according to the first embodiment of the present invention. As shown in FIG. 3, regenerative resistors 27 are provided at the bottom of the CT apparatus 1. The regenerative resistors 27 are partially provided inside a gantry stand 12" and partially project from the bottom of the CT apparatus 1. A bottom surface of the CT apparatus 1 and the gantry stand 12" is processed so as to fit the regenerative resistors 27. Bottom surfaces of the regenerative resistors 27 against a floor H have a predetermined constant curvature. Similar to the first modification, the floor H where the CT apparatus 1 is placed is processed to accommodate the projecting regenerative resistors 27.

In the above configuration of the CT apparatus 1 with the fitting floor H, the regenerative resistors 27 contact the floor H in a larger contact area than the regenerative resistors 7 in FIG. 1. Therefore, the heat generated by the regenerative resistors 27 can be transferred more efficiently to the floor H.

The curvature of the bottom surfaces of the regenerative resistors 27 is not necessarily constant. Each of the regenerative resistors 27 may have an independent curvature. Alternatively, some of the regenerative resistors 27 may have either a common curvature or respective independent curvatures while the rest of the regenerative resistors 27 do not have any curvature, as shown in FIG. 2. The bottom surfaces of the regenerative resistors 27 may be processed in a corrugated form. The curvature may be positive and/or negative. In any case of the above alternatives, the floor H is configured to fit with the regenerative resistors 27. Otherwise, the floor H needs to have dents large enough to contain the projecting regenerative resistors 27.

According to the first embodiment of the present invention, the first modification, and the second modification may be combined. Regenerative resistors may be placed as shown in FIG. 2 and have the shape as described in the second modification. This combination makes it possible that the regenerative resistors have a further larger area to contact with a floor. Better conduction efficiency can be realized in the above combination.

(Second Embodiment)

Figure 4:
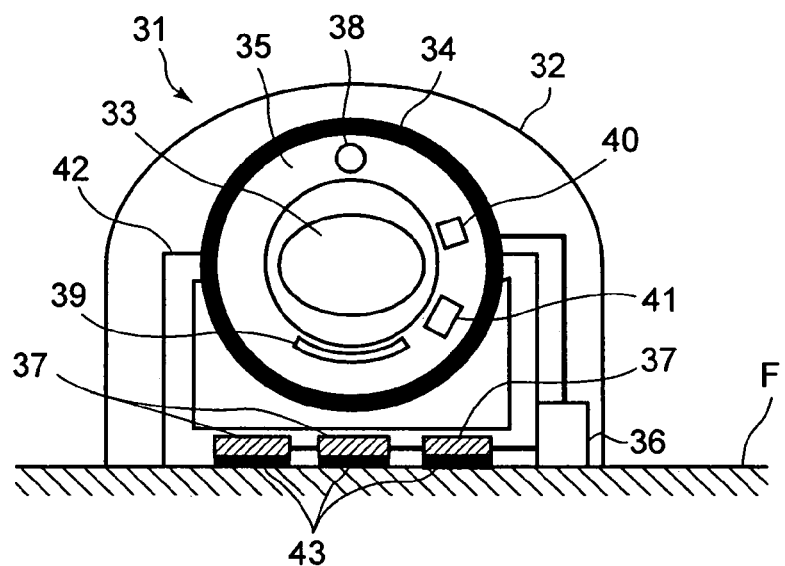
FIG. 4 is an illustration showing an exemplary configuration of a CT apparatus according to a second embodiment of the present invention.

FIG. 4 is an illustration showing an exemplary configuration of a CT apparatus 31 according to a non-limiting second embodiment of the present invention. FIG. 4 shows a perspective view from a front of the CT apparatus 31. Similar to the CT apparatus 1 shown in FIG. 1, the CT apparatus 31 includes a body 32, a tomography opening 33, a motor 34, a rotation ring 35, a servo-amplifier 36, regenerative resistors 37, an X-ray tube 38, a detector 39, a power source unit 40, a signal processor 41, and a gantry stand 42. The CT apparatus 31 is placed on the floor F.

Operations of the above-mentioned units of the CT apparatus 31 are similar to those given the same names of the CT apparatus 1. Therefore, details of such operations are omitted herein, except for the regenerative resistors 37.

The regenerative resistors 37 are inserted into and placed in an opening space of the gantry stand 42. Accordingly, heat generated by the regenerative resistors 37 is efficiently emitted through the gantry stand 42.

According to the second embodiment of the present invention, the CT apparatus 31 further includes heat conductive members 43. The heat conductive members 43 conduct the heat generated by the regenerative resistors 37. The heat conductive members 43 can be made of a material having high heat conductivity, such as, for example, metal. Iron may be one example of the metal. Further, the heat conductive members 43 may also preferably include a heat-resistant material since the regenerative resistors 37 usually reach a quite high temperature (e.g., 70 degrees Celsius). Similar to the regenerative resistors 37, the heat conductive members 43 are also inserted into and placed in the opening space of the gantry stand 42. Top surfaces of the heat conductive members 43 contact bottom surfaces of the regenerative resistors 37. A top surface of each heat conductive member 43 is not limited to, but may have an area identical to that of a bottom surface of each regenerative resistor 37. Bottom surfaces of the heat conductive members 43 contact the floor F.

Since the heat generated by the regenerative resistors 37 is emitted to the floor F through the heat conductive members 43, the heat conduction efficiency between the regenerative resistors 37 and the floor F may be improved, compared to a case of a direct contact between the regenerative resistors 37 and the floor F.

(Third Modification)

Figure 5A:
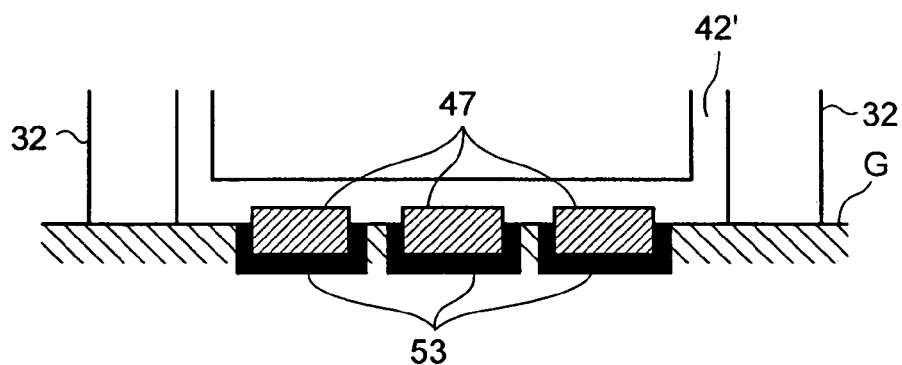
FIG. 5A is an illustration showing a third modified configuration example of the CT apparatus according to the second embodiment of the present invention.

Heat conductive members are provided to the regenerative resistors in a different manner from the heat conductive members 43 shown in FIG. 4. FIG. 5A is an illustration showing a third non-limiting modified configuration example of the CT apparatus according to the second embodiment of the present invention.

As shown in FIG. 5A, regenerative resistors 47 are provided at the bottom of the CT apparatus 31. A part of the regenerative resistors 47 is provided inside a gantry stand 42' and the rest projects from the bottom of the CT apparatus 31. A bottom surface of the CT apparatus 31 and the gantry stand 42' are processed to fit the regenerative resistors 47. Surfaces of the regenerative resistors 47, which correspond to the rest projecting from the bottom of the CT apparatus 31, are covered by heat conductive members 53. A floor G where the CT apparatus 31 is placed is processed to fit the heat conductive members 53 covering the projecting regenerative resistors 47.

In the above configuration of the CT apparatus 31 with the fitting floor G, the regenerative resistors 47 contact the heat conductive members 53 in a larger contact area than the regenerative resistors 37 in FIG. 4. Therefore, the heat generated by the regenerative resistors 47 can be transferred more efficiently to the heat conductive members 53. The heat conductive members 53 contact the floor G in a larger contact area than the heat conductive members 43 in FIG. 4. Therefore, the heat generated by the regenerative resistors 47 can be transferred (or emitted) more efficiently through the heat conductive members 53 to the floor G. Further, a part of the heat generated by the regenerative resistors 47 is emitted through the gantry stand 42'.

Figure 5B:
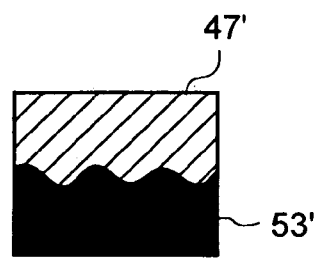
FIG. 5B is an illustration showing an exemplary surface of a regenerative resistor and a corresponding surface of a heat conductive member according to the second embodiment of the present invention.

FIG. 5B is an illustration showing an exemplary surface of a regenerative resistor and a corresponding surface of a heat conductive member according to the second non-limiting embodiment of the present invention. As shown in FIG. 5B, a regenerative resistor 47' has a surface (e.g., a bottom surface or a side surface) processed in a corrugated form. Correspondingly, a heat conductive member 53' contacting the regenerative resistor 47' has a surface also processed in a corrugated form to fit the surface of the regenerative resistor 47'.

Accordingly, the regenerative resistor 47' can contact the heat conductive member 53' in a larger contact area to transfer the generated heat more efficiently. An opposite surface of the heat conductive member 53' is not limited to, but may be processed in a non-corrugated form as similar to the heat conductive members 53 in FIG. 5A. Therefore, compared to the second modification of the first embodiment, it is not necessary to prepare the floor G in a complicated form to fit the corrugated surface of the regenerative resistor 47', since the regenerative resistor 47' is covered by the heat conductive member 53'. The surfaces of the regenerative resistor 47' and the heat conductive member 53' are not limited to the corrugated form, but may alternatively be in any form, such as, for example, a convexo-concave relation form, as appropriate, considering an amount of generating heat energy or the like.

According to the third non-limiting modification, the regenerative resistors 47 shown in FIG. 5A may alternatively fully project from the CT apparatus 31. In this case, top surfaces of the regenerative resistors 47 contact with the bottom surface of the CT apparatus 31. The heat conductive members 53 may cover all the surfaces of the regenerative resistors 47, except for the top surfaces contacting the bottom surface of the CT apparatus 31.

(Fourth Modification)

Figure 6:
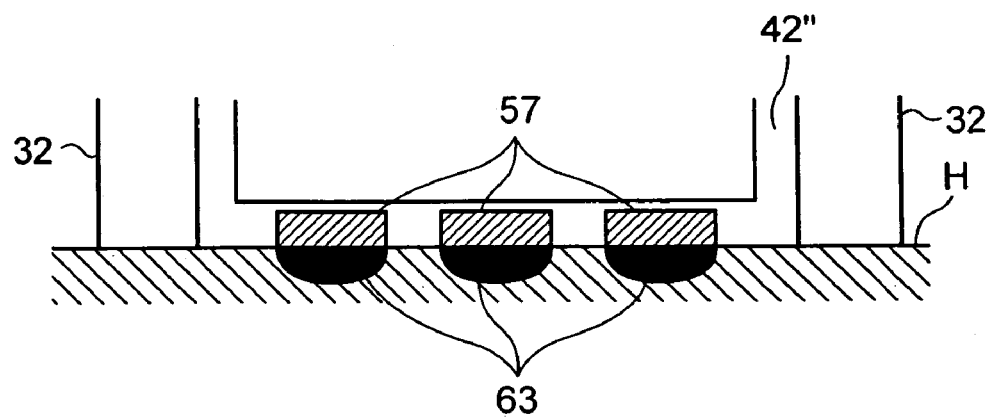
FIG. 6 is an illustration showing a fourth modified configuration example of the CT apparatus according to the second embodiment of the present invention.

Further modification of the CT apparatus 31 will be described with reference to FIG. 6. FIG. 6 is an illustration showing a fourth non-limiting modified configuration example of the CT apparatus according to the second embodiment of the present invention. As shown in FIG. 6, regenerative resistors 57 are provided at the bottom of the CT apparatus 31. The regenerative resistors 57 are provided inside a gantry stand 42" and contact heat conductive members 63 at their bottom surfaces. The contacted heat conductive members 63 project from the bottom of the CT apparatus 31. Bottom surfaces (through side surfaces) of the heat conductive members 63 against a floor H have a predetermined constant curvature. The floor H where the CT apparatus 31 is placed is processed so as to fit the projecting heat conductive members 63.

In the above configuration of the CT apparatus 31 with the fitting floor H, the heat conductive members 63 contact the floor H in a large contact area. Therefore, the heat generated by the regenerative resistors 57 can be transferred more efficiently through the heat conductive members 63 to the floor H.

The curvature of the surfaces of the heat conductive members 63 is not necessarily constant. Each of the heat conductive members 63 may have an independent curvature. Alternatively, some of the heat conductive members 63 may have either a common curvature or respective independent curvatures while the rest of the heat conductive members 63 do not have any curvature. The surfaces of the heat conductive members 63 may be processed in a corrugated form. The curvature may be positive and/or negative. Surface shapes of the heat conductive members 63 may be designed in any form, if necessary. In any case of the above alternatives, the floor H should have a shape to fit the heat conductive members 63. Otherwise, the floor H needs to have dents large enough to contain the projecting heat conductive members 63.

According to the second embodiment of the present invention, the third modification and the fourth modification may be combined. Regenerative resistors may be placed as shown in FIG. 6 and may contact heat conductive members in a corrugated form as shown in FIG. 5B. This combination makes it possible for regenerative resistors to have a larger area to contact the heat conductive members, which has a larger area to contact a floor. Therefore, the heat generated by the regenerative resistors is emitted more efficiently through the heat conductive members to the floor.

(Fifth Modification)

Figure 7:
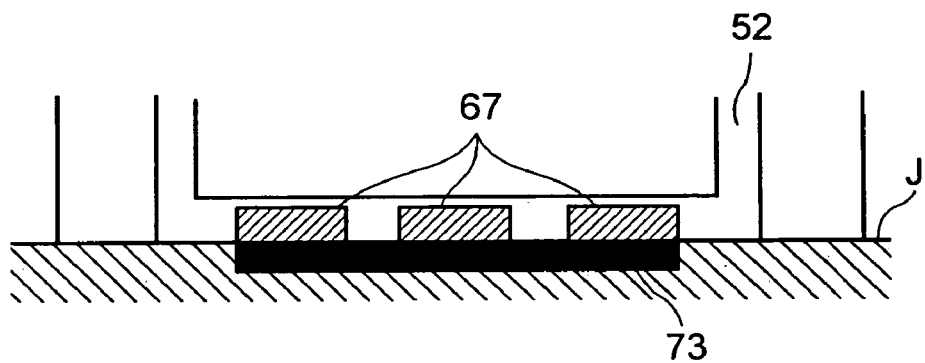
FIG. 7 is an illustration showing a fifth modified configuration example of the CT apparatus according to the second embodiment of the present invention.

Further non-limiting modification of the CT apparatus 31 will be described with reference to FIG. 7. Each one heat conductive member is not needed to be assigned for each one regenerative resistor. FIG. 7 is an illustration showing a fifth modified configuration example of the CT apparatus according to the second embodiment of the present invention.

As shown in FIG. 7, only one heat conductive member 73 is provided for regenerative resistors 67. The regenerative resistors 67 are provided at the bottom of the CT apparatus 31. The regenerative resistors 67 are provided inside the gantry stand 52. A top surface of the heat conductive member 73 partially contacts bottom surfaces of the regenerative resistors 67 and partially contacts a part of a bottom surface of the CT apparatus 31.

The heat conductive member 73 projects from the bottom of the CT apparatus 31. The heat conductive member 73 may alternatively be used in common only with some of the regenerative resistors 67. Still alternatively, one large heat conductive member 73 may be used in common with some of the regenerative resistors 67 while other regenerative resistors 67 may be provided with independent heat conductive members 73, respectively. As a further alternative example of the fifth modification, both the regenerative resistors 67 and the heat conductive member(s) 73 may be provided in the gantry stand 52. A bottom surface of the CT apparatus 31 and the gantry stand 52 are processed to fit the regenerative resistors 67. A floor J where the CT apparatus 31 is placed is processed to fit the projecting heat conductive member 73. Therefore, bottom and side surfaces of the heat conductive member 73 contact the floor J to transfer the heat generated by the regenerative resistors 67 to the floor J. To obtain a larger contact area with the floor J, the bottom (and/or side) surface of the heat conductive member 73 against the floor J may have a predetermined constant curvature or any other form as described before.

(Sixth Modification)

Figure 8:
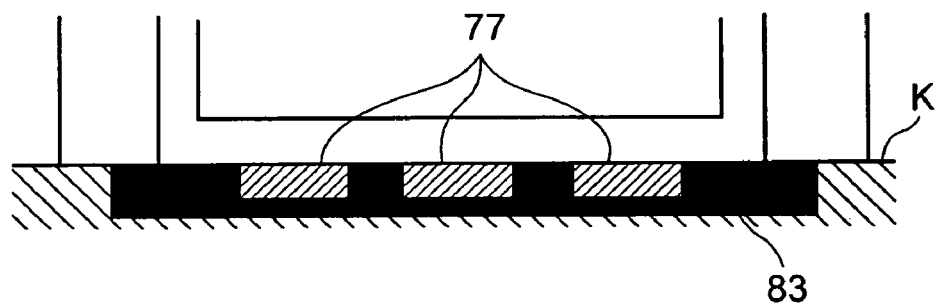
FIG. 8 is an illustration showing a sixth modified configuration example of the CT apparatus according to the second embodiment of the present invention.

Still further modification of the CT apparatus 31 will be described with reference to FIG. 8. FIG. 8 is an illustration showing a sixth non-limiting modified configuration example of the CT apparatus according to the second embodiment of the present invention. As shown in FIG. 8, only one heat conductive member 83 is provided for regenerative resistors 77. The regenerative resistors 67 are provided at the bottom of the CT apparatus 31 and project from the bottom surface of the CT apparatus 31. The heat conductive member 83 covers bottom and side surfaces of the regenerative resistors 77 and contacts a part of a bottom surface of the CT apparatus 31.

The regenerative resistors 77 may alternatively be provided partially in a gantry stand and may partially project from the bottom surface of the CT apparatus 31. Still alternatively, one large heat conductive member 83 may be used in common with some of the regenerative resistors 77 while other regenerative resistors 77 may be provided with and covered by independent heat conductive members 83, respectively.

A floor K where the CT apparatus 31 is placed is processed to fit the projecting heat conductive member 83. Therefore, bottom and side surfaces of the heat conductive member 83 contact the floor K to transfer the heat generated by the regenerative resistors 77 to the floor K. To obtain a larger contact area with the floor K, the bottom (and/or side) surface of the heat conductive member 83 against the floor K may have a predetermined constant curvature or any other form as described before.

(Seventh Modification)

Figure 9:
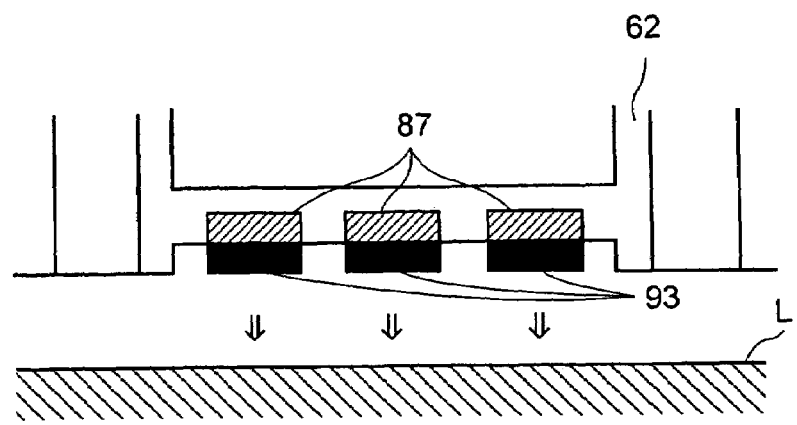
FIG. 9 is an illustration showing a seventh modified configuration example of the CT apparatus according to the second embodiment of the present invention.

FIG. 9 is an illustration showing a non-limiting seventh modified configuration example of the CT apparatus according to the second embodiment of the present invention. As shown in FIG. 9, there is a concave dent 90 at the bottom of the CT apparatus 31. Regenerative resistors 87 are provided in a gantry stand 62. Bottom surfaces of the regenerative resistors 87 contact heat conductive members 93, which are provided in the concave dent 90. The height of the heat conductive members 93 is the same as the height of the concave dent 90. Therefore, bottom surfaces of the heat conductive members 93 can contact a floor L to transfer the heat generated by the regenerative resistors 87 to the floor L.

Alternatively, only one heat conductive member 93 may be used in common with the regenerative resistors 87. The regenerative resistors 87 may alternatively be provided partially in the gantry stand 62 and may partially project from a surface of the concave dent 90. According to the seventh modification, there is no need to process the floor L for the contact with the heat conductive members 93, which is advantageous.

Similar to the first embodiment, according to the second embodiment, the contact of the regenerative resistors with the floor through the heat conductive members makes it possible to more efficiently emit the heat to the outside of the CT apparatus 31. Further, placing the regenerative resistors a predetermined distance away from the sides of the body can be helpful for reducing a risk that the doctor, the radiological technologist, or the field engineer touches the regenerative resistors by accident and is burned. Still further, it may be possible to provide regenerative resistors in a bottom empty space of the CT apparatus (or the gantry stand) without changing other unit positions.

Further, the first embodiment and the second embodiment may be combined with regard to use of regenerative resistors and heat conductive members. In other words, for example, some regenerative resistors may directly contact a floor while the rest of the regenerative resistors indirectly contact the floor through heat conductive members, if necessary.

(Third Embodiment)

Figure 10:
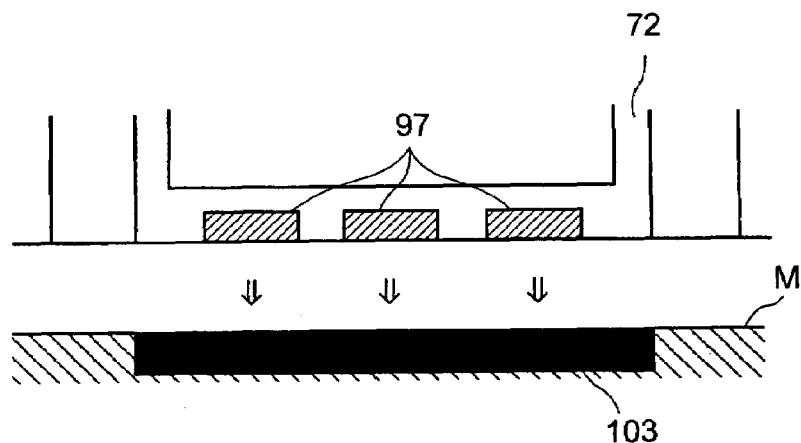
FIG. 10 is an illustration showing a first exemplary relationship between regenerative resistors and heat conductive members according to a third embodiment of the present invention.

A heat conductive member can be provided as a part of a floor according to a third non-limiting embodiment of the present invention. FIG. 10 is an illustration showing a first exemplary relationship between regenerative resistors and a heat conductive member according to a third embodiment of the present invention.

As shown in FIG. 10, a heat conductive member 103 is dug into a floor M and provided as a part of the floor M. A top surface of the heat conductive member 103 is includes a part of a surface of the floor M. Regenerative resistors 97 are provided at the bottom of the CT apparatus 31. The regenerative resistors 97 are provided inside a gantry stand 72. A bottom surface of the CT apparatus 31 and the gantry stand 72 is processed so as to fit the regenerative resistors 97.

When the CT apparatus 31 is placed on the heat conductive member 103 of the floor M, the top surface of the heat conductive member 103 contacts bottom surfaces of the regenerative resistors 97 and a part of a bottom surface of the CT apparatus 31. Therefore, the heat generated by the regenerative resistors 97 is transferred to the floor M through the heat conductive member 103.

(Eighth Modification)

Figure 11:
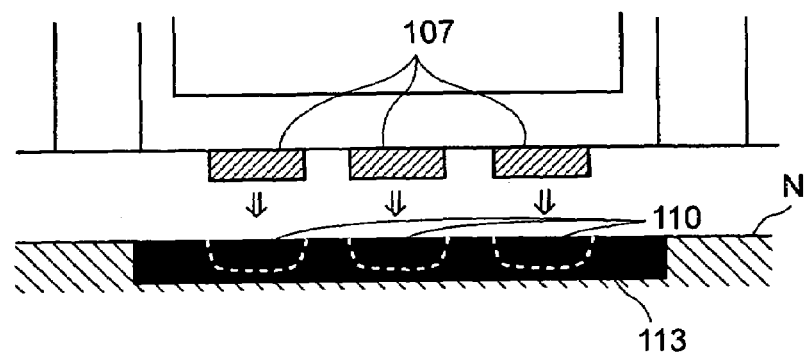
FIG. 11 is an illustration showing an eighth modified configuration example of the CT apparatus according to the third embodiment of the present invention.

FIG. 11 is an illustration showing an eighth modified configuration example of the CT apparatus according to the third embodiment of the present invention.

As shown in FIG. 11, a heat conductive member 113 is dug into a floor N and provided as a part of the floor N. A top surface of the heat conductive member 113 includes a part of a surface of the floor N. Further, the heat conductive member 113 is made of elastic material(s). Regenerative resistors 107 are provided at the bottom of the CT apparatus 31 and project from a bottom surface of the CT apparatus 31. When the CT apparatus 31 is placed on the heat conductive member 113 of the floor N, a part 110 of the top surface of the heat conductive member 113 is dented downward due to the weight of the CT apparatus 31 in accordance with the shape of the projecting regenerative resistors 107. Accordingly, bottom and side surfaces of the regenerative resistors 107 contact the heat conductive member 113. Therefore, the heat generated by the regenerative resistors 107 is transferred to the floor N through the heat conductive member 113.

Figure 12A:
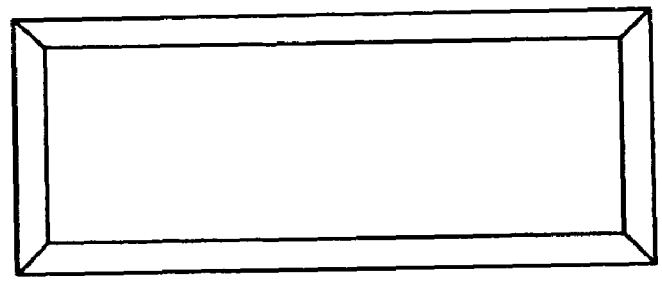
FIG. 12A is an illustration showing an exemplary top view of a regenerative resistor according to the embodiments of the present invention.
Figure 12B:
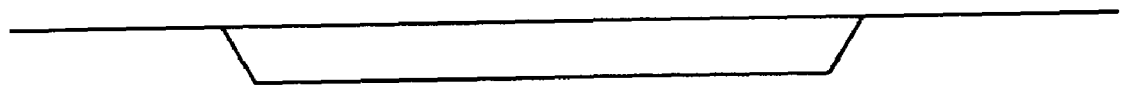
FIG. 12B is an illustration showing an exemplary side view of the regenerative resistor according to the embodiments of the present invention.

FIG. 12A is an illustration showing an example of a regenerative resistor according to the embodiments of the present invention. The size of the regenerative resistor is typically around 10 cm×30 cm with a thickness of 3 cm to 5 cm. Further, a typical regenerative resistor is in a trapezoidal form and wrapped or coated by aluminum except for its upper base. In a use of such regenerative resistors, the upper base with a cement surface is used as a bottom surface of the regenerative resistors to contact with a heat conductive member or a floor as shown in FIG. 12B.

Figure 12C:
FIG. 12C is an illustration showing an exemplary cement surface view of the regenerative resistor according to the embodiments of the present invention.

To describe the bottom surface (i.e., the upper base) precisely, the bottom surface is not flat due to the cement as shown in FIG. 12C. Therefore, it is preferable to use a heat conductive member which can be fit to the non-flat bottom surface of the regenerative resistor. One possible solution is to use an elastic material, if applicable. Another possible solution is to apply a conductive material on the non-flat bottom surface of the regenerative resistor, if applicable. The solution-implemented regenerative resistor can contact a heat conductive member as described before. (Note that these solutions are preferable but not essential to obtain advantages according to the embodiments of the present invention.)

According to the embodiments of the present invention, the number of the regenerative resistors is not limited to a particular number, but may be any number, including a case of a single use.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. An X-ray computed tomography apparatus, wherein an X-ray is generated by a generator and X-ray data resulting from the X-ray is detected by a detector, the apparatus comprising:

a supporter configured to support the generator and the detector;

a driver configured to generate regenerative energy and to drive the supporter;

a body configured to incorporate the supporter and the driver; and a converter provided at a bottom of the body and configured to convert the regenerative energy caused by the driver to heat energy, wherein the converter is further configured to project from the bottom of the body, and the converter is further configured to contact a floor, and the floor is processed to fit the converter.

2. An X-ray computed tomography apparatus, wherein an X-ray is generated by a generator and X-ray data resulting from the X-ray is detected by a detector, the apparatus comprising:
- a supporter configured to support the generator and the detector;
- a driver configured to generate regenerative energy and to drive the supporter;
- a body configured to incorporate the supporter and the driver; and
- a converter provided at a bottom of the body and configured to convert the regenerative energy caused by the driver to heat energy, wherein
- the converter is further configured to project from the bottom of the body, and
- the converter is further configured to contact a floor, and the floor is processed to contain the converter.

3. An X-ray computed tomography apparatus, wherein an X-ray is generated by a generator and X-ray data resulting from the X-ray is detected by a detector, the apparatus comprising:
- a supporter configured to support the generator and the detector;
- a driver configured to generate regenerative energy and to drive the supporter;
- a body configured to incorporate the supporter and the driver; and
- a converter provided at a bottom of the body and configured to convert the regenerative energy caused by the driver to heat energy, wherein
- the converter is configured to contact a floor, and
- the converter includes a plurality of converter members, at least two of the plurality of converter members each having a surface with a common curvature that is configured to contact the floor.

4. An X-ray computed tomography apparatus, wherein an X-ray is generated by a generator and X-ray data resulting from the X-ray is detected by a detector, the apparatus comprising:
- a supporter configured to support the generator and the detector;
- a driver configured to generate regenerative energy and to drive the supporter;
- a body configured to incorporate the supporter and the driver; and
- a converter provided at a bottom of the body and configured to convert the regenerative energy caused by the driver to heat energy, wherein
- the converter is configured to contact a floor, and
- the converter includes a plurality of converter members, at least two of the plurality of converter members having a surface with an independent curvature that is configured to contact the floor.

5. An X-ray computed tomography apparatus, wherein an X-ray is generated by a generator and X-ray data resulting from the X-ray is detected by a detector, the apparatus comprising:
- a supporter configured to support the generator and the detector;
- a driver configured to generate regenerative energy and to drive the supporter;
- a body configured to incorporate the supporter and the driver;
- a converter provided at a bottom of the body and configured to convert the regenerative energy caused by the driver to heat energy; and
- at least one heat conductive member, wherein
- the converter is configured to contact a floor through the at least one heat conductive member, and
- a surface of the converter has a first curvature and a surface of the at least one heat conductive member has a second curvature corresponding to the first curvature, the surface of the converter contacting the surface of the at least one heat conductive member.

6. The apparatus according to claim 5, wherein the surface of the converter and the surface of the at least one heat conductive member include at least one corrugated portion, respectively.

7. An X-ray computed tomography apparatus, wherein an X-ray is generated by a generator and X-ray data resulting from the X-ray is detected by a detector, the apparatus comprising:
- a supporter configured to support the generator and the detector;
- a driver configured to generate regenerative energy and to drive the supporter;
- a body configured to incorporate the supporter and the driver;
- a converter provided at a bottom of the body and configured to convert the regenerative energy caused by the driver to heat energy; and
- at least one heat conductive member, wherein
- the converter is configured to contact a floor through the at least one heat conductive member,
- the at least one heat conductive member is configured to project from the bottom of the body, and
- the floor is processed to fit the at least one heat conductive member.

8. An X-ray computed tomography apparatus, wherein an X-ray is generated by a generator and X-ray data resulting from the X-ray is detected by a detector, the apparatus comprising:
- a supporter configured to support the generator and the detector;
- a driver configured to generate regenerative energy and to drive the supporter;
- a body configured to incorporate the supporter and the driver;
- a converter provided at a bottom of the body and configured to convert the regenerative energy caused by the driver to heat energy; and
- at least one heat conductive member, wherein
- the converter is configured to contact a floor through the at least one heat conductive member,
- the at least one heat conductive member is configured to project from the bottom of the body, and
- the floor is processed to contain the at least one heat conductive member.

* * * * *